(12) United States Patent
Keller et al.

(10) Patent No.: US 10,667,782 B2
(45) Date of Patent: Jun. 2, 2020

(54) STETHOSCOPE

(71) Applicant: 3M INNOVATIVE PROPERTIES COMPANY, St. Paul, MN (US)

(72) Inventors: Joseph P. Keller, Wahpeton, ND (US); Robert S. Kody, Woodbury, MN (US); Daniel J. Rogers, Grant, MN (US); Raymond L. Watrous, Belle Mead, NJ (US)

(73) Assignee: 3M Innovative Properties Company, Saint Paul, MN (US)

( * ) Notice: Subject to any disclaimer, the term of this patent is extended or adjusted under 35 U.S.C. 154(b) by 268 days.

(21) Appl. No.: 15/567,316

(22) PCT Filed: May 5, 2016

(86) PCT No.: PCT/US2016/030877
§ 371 (c)(1),
(2) Date: Oct. 17, 2017

(87) PCT Pub. No.: WO2016/186849
PCT Pub. Date: Nov. 24, 2016

(65) Prior Publication Data
US 2018/0085086 A1    Mar. 29, 2018

Related U.S. Application Data

(60) Provisional application No. 62/162,120, filed on May 15, 2015.

(51) Int. Cl.
*A61B 7/02* (2006.01)

(52) U.S. Cl.
CPC ..................... *A61B 7/02* (2013.01)

(58) Field of Classification Search
CPC .............. A61B 7/02; A61B 7/026; A61B 7/04
USPC ......................................................... 181/131
See application file for complete search history.

(56) References Cited

U.S. PATENT DOCUMENTS

| | | |
|---|---|---|
| 2,363,686 A | 11/1944 | Olson |
| 3,437,172 A | 4/1969 | Allen |
| 3,493,075 A | 2/1970 | Mendelson |
| 3,614,991 A | 10/1971 | Machlup |
| 4,200,169 A | 4/1980 | MacDonald, III |
| 4,461,368 A * | 7/1984 | Plourde ................... A61B 7/02 181/131 |
| 4,823,906 A * | 4/1989 | Gabriel ................. A61B 7/026 181/131 |
| 4,852,684 A | 8/1989 | Packard |
| 4,867,268 A * | 9/1989 | Ulert ........................ A61B 7/02 181/137 |
| 4,913,259 A | 4/1990 | Packard |
| 4,991,686 A | 2/1991 | Allen |
| 5,449,865 A | 9/1995 | Desnick |

(Continued)

OTHER PUBLICATIONS

International Search Report for PCT International Application No. PCT/US2016/030877, dated Jul. 22, 2016, 5pgs.

*Primary Examiner* — Forrest M Phillips
(74) *Attorney, Agent, or Firm* — 3M Innovative Properties Company; Jonathan V. Sry

(57) ABSTRACT

A stethoscope includes a flexible chest piece including a top surface, a bottom surface, a side surface defining a slope between the top surface and the bottom surface, and a groove extending along an inner circumference of the chest piece. A diaphragm is positioned within the groove.

24 Claims, 8 Drawing Sheets

(56) References Cited

U.S. PATENT DOCUMENTS 5,945,640 A * 8/1999 Rossini .................. A61B 7/026
 181/131
6,523,639 B1 * 2/2003 Shieh ....................... A61B 7/02
 181/131

* cited by examiner

STETHOSCOPE

FIELD OF THE INVENTION

The present invention relates generally to stethoscopes. More particularly, the present invention relates to a low cost, single-use or single-patient stethoscope.

BACKGROUND

The majority of current day stethoscopes are used for a number of years, with individual clinicians using the same stethoscope day after day on multiple patients. Clinicians may choose to use the same stethoscope for many years for familiarity, but also for cost concerns. Current designs of stethoscopes having high acoustic quality can come at a high cost, with the two most expensive components of stethoscopes being the chest piece and the head set. Most, if not all, stethoscopes currently sold include a chest piece with the tubing extending from a side surface of the bell of the chest piece such that the tubing is positioned parallel to the diaphragm. An example of a typical current day stethoscope chest pieces is illustrated in FIG. 1.

Another factor which figures into the cost of current day stethoscopes include attachment of the diaphragm to the chest piece. The diaphragms currently used on most stethoscopes are made of two pieces, the diaphragm and the rim. The rim is used to hold the diaphragm on the chest piece. While this construction works very well to hold the components on the chest piece, the process for manufacturing the two piece rim/diaphragm construction requires numerous operations to produce the assembled rim/diaphragm constructions. Generally, separate operations are needed to manually mold the diaphragms, to manually mold the rims, to manually trim runners from diaphragms, to manually assemble the diaphragms into the rims positioned on the chest piece, and to inspect all assembled products.

While so-called disposable or single-use stethoscopes, such as, for example the Welch Allyn Uniscope disposable stethoscope, are available at a low cost, the sound quality of these stethoscopes is often not accepted by clinicians due to the materials and construction.

SUMMARY

In one embodiment, the present invention is a stethoscope. The stethoscope includes a flexible chest piece including a top surface, a bottom surface, a side surface defining a slope between the top surface and the bottom surface, and a groove extending along an inner circumference of the chest piece. A diaphragm is positioned within the groove.

In another embodiment, the present invention is an acoustic stethoscope including a flexible chest piece, a diaphragm and tubing. The flexible chest piece includes a top surface, a bottom surface, a side surface defining a slope between the top surface and the bottom surface, and a groove along an inner circumference of the chest piece. The groove is proximate the bottom surface of the chest piece. The diaphragm is positioned within the groove. The tubing is connected to the top surface of the flexible chest piece, wherein the tubing and the chest piece are a unitary piece.

In yet another embodiment, the present invention is an acoustic stethoscope. The acoustic stethoscope includes a flexible chest piece including a top surface, a bottom surface, a side surface defining a slope between the top surface and the bottom surface, and a groove extending along an inner circumference of the chest piece. The groove is positioned between about 0.005 inches (0.13 millimeters) and about 0.175 inches 4.45 millimeters) from the bottom surface. Tubing extends substantially perpendicularly from the top surface of the flexible chest piece.

BRIEF DESCRIPTION OF THE DRAWINGS

These figures are not drawn to scale and are intended merely for illustrative purposes.

DETAILED DESCRIPTION

The present invention is a low cost, single-use or single-patient stethoscope. In one embodiment, the stethoscope is a tunable stethoscope. A primary advantage of the low cost, single-use or single-patient stethoscope is the decreased cost of the stethoscope. Due to the replacement of various parts of a conventional stethoscope with alternative materials, designs, and configurations, an economical stethoscope with high acoustic quality is presented. The low cost, single-use or single-patient stethoscope of the present invention makes it economical for a stethoscope to be used only once or only to treat one patient before being discarded, reprocessed or recycled. The low cost, single-use or single-patient stethoscope can be easily produced at low cost such that treating patients with contagious diseases becomes feasible without sacrificing the acoustic diagnostic capabilities of the more current, expensive stethoscopes.

Figure 1:
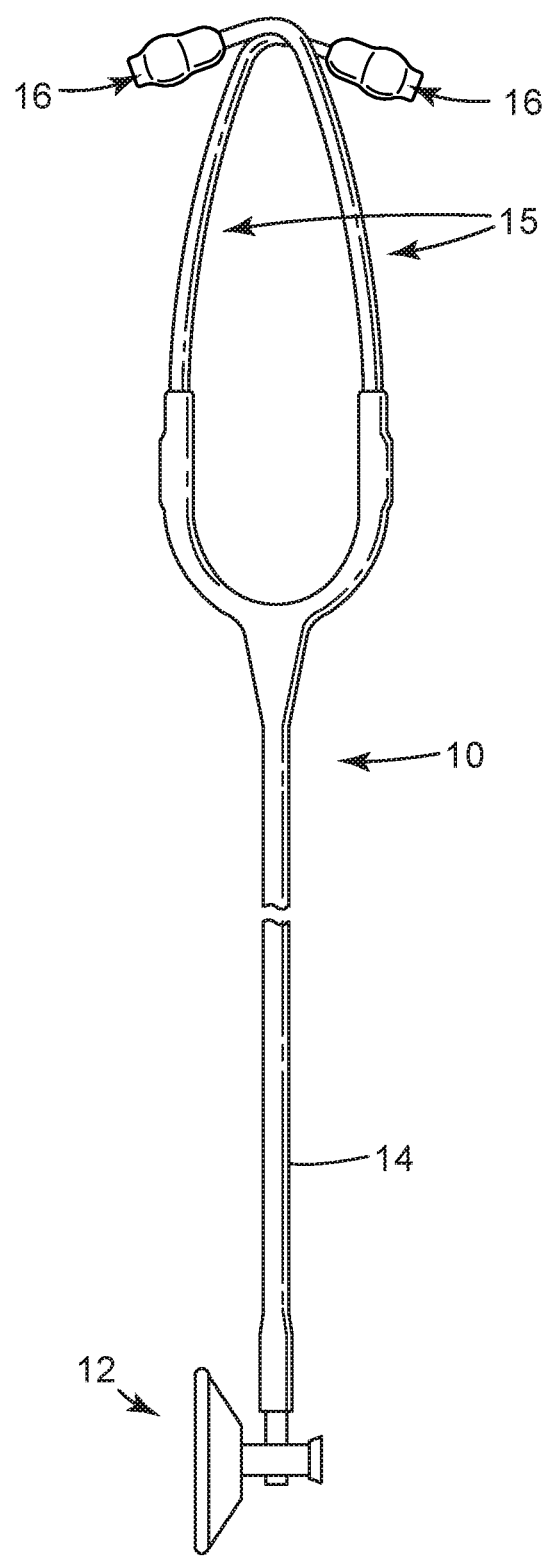
FIG. 1 is a side view of a prior art stethoscope.
Figure 2:
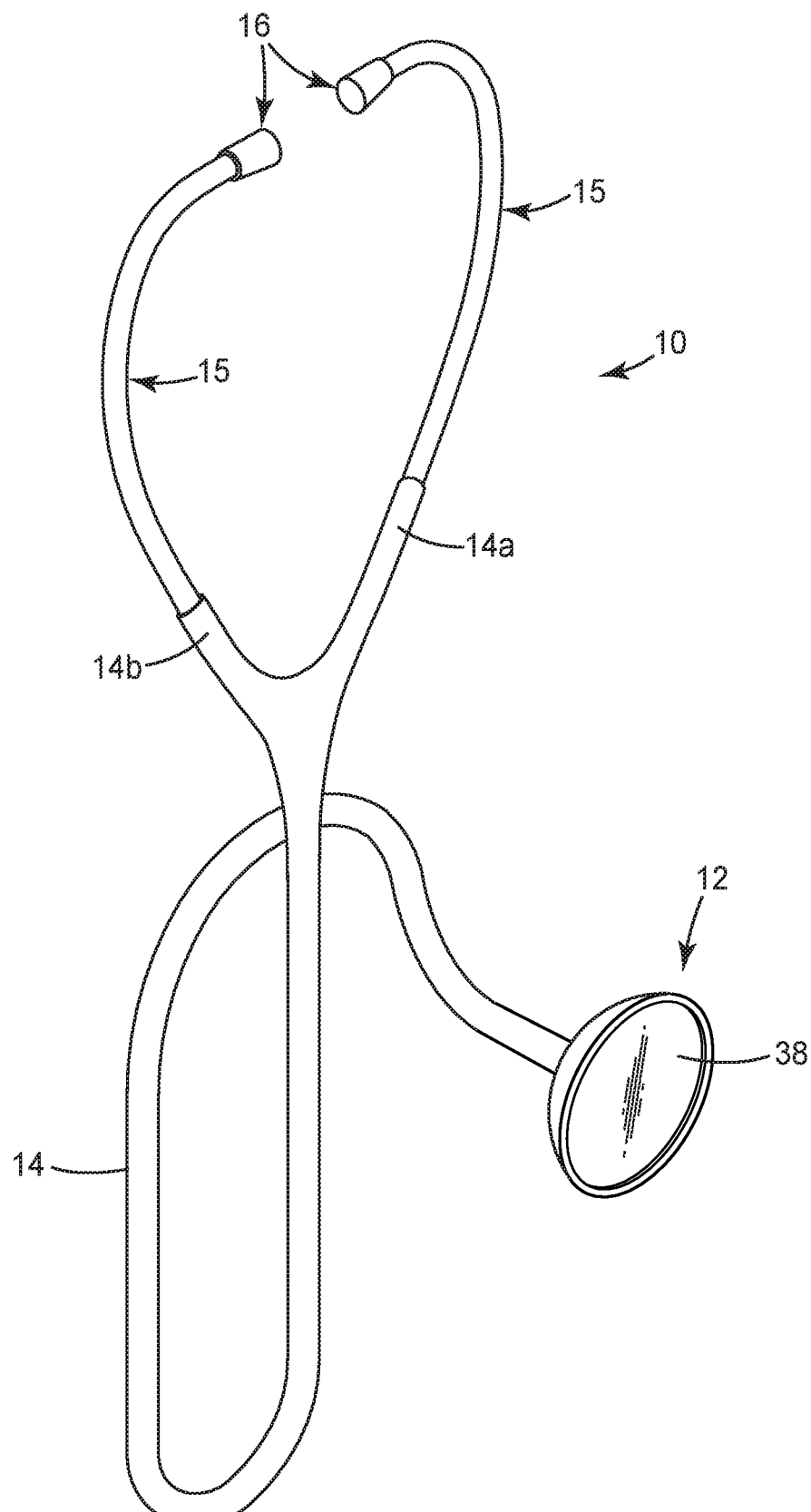
FIG. 2 is a perspective view of a low cost, single-use or single-patient stethoscope of the present invention.

FIG. 2 shows a perspective view of the low cost, single-use or single-patient stethoscope 10 of the present invention. The stethoscope 10 includes a chest piece 12 and elongated tubing 14 attached to binaural ear tubes 15 and terminating with ear tips 16. The elongated tubing 14 splits into flexible tubings 14a and 14b that run to the ear tips 16 via the binaural ear tubes 15. The chest piece 12 and the flexible tubing 14 are integrally formed and are made of a flexible material. In one embodiment, the chest piece 12 and the tubing 14 have a Shore A hardness durometer of between about 30 and about 100, particularly between about 30 and about 90, more particularly between about 40 and about 75, and even more particularly between about 50 and about 60. In one embodiment, the chest piece 12 and the tubing 14 are formed of a polymeric material. An example of a suitable polymeric material includes, but is not limited to, polyvinyl chloride. In one embodiment, the tubing 14 may have a thickness of between about 0.04 inches (1.02 mm) and about 0.25 inches (6.35 mm), particularly between about 0.1 inches and about 0.175 inches (2.54 mm and about 4.45 mm), and more particularly about 0.125 inches (3.18 mm). The chest piece 12 and the tubing 14 may be made, for example, using a dip molding process.

Figure 3:
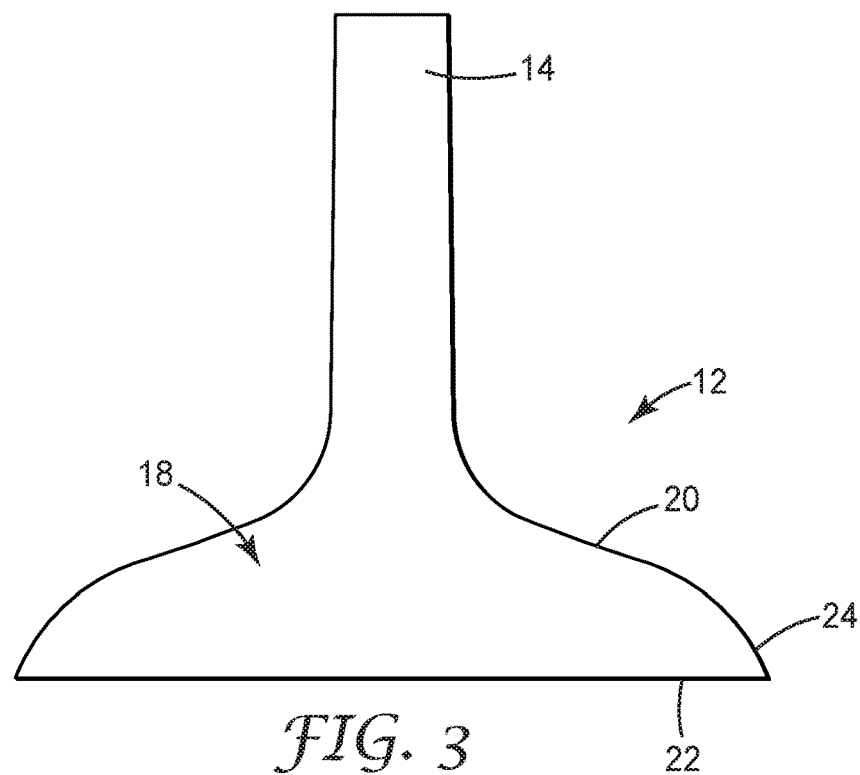
FIG. 3 is a side view of a chest piece of the low cost, single-use or single-patient stethoscope of the present invention.

FIG. 3 shows a side view of the chest piece 12 and the tubing 14 of the stethoscope 10 of the present invention. The chest piece 12 includes a substantially dome-like portion 18 having a top surface 20, a bottom surface 22, and side surface 24. The side surfaces 24 slope away convexly from the top surface 20 toward the bottom surface 22 to form the dome 18. In one embodiment, when the top surface 20 is relatively flat, an angle, or slope, may be measured between the top and bottom surfaces 20 and 22, respectively, of up to about 45°, particularly up to about 30°, and more particularly up to about 15°. In one an angle of about 7° may be present between the top and bottom surfaces 20 and 22. In one embodiment, the dome-like portion 18 has a wall thickness of between about 0.04 inches (1.02 mm) and about 0.4 inches (10.16 mm), particularly between about 0.1 inches (2.54 mm) and about 0.3 inches (7.62 mm), and more particularly about 0.2 inches (5.08 mm). Although the specification describes, and the figures depict, the shape of the chest piece 12 to be dome-shaped, the chest piece may have various other shapes known to those of skill in the art. For example, the chest piece 12 may be conical, cylindrical, polygonal or faceted, with an interior chamber volume and shape adjusted to optimize acoustic performance of the low cost, single-use or single-patient stethoscope 10.

As can be seen in FIGS. 2 and 3, the tubing 14 extends substantially perpendicularly from the top surface 20 of the chest piece 12. In one embodiment, the tubing 14 may extend at an angle other than about 90° from the top surface 20 of the chest piece 12. In practice, the clinician may grasp the stethoscope 10 where the tubing 14 meets the chest piece 12 and position the bottom surface 22 of the chest piece 12 against the body of the patient to listen to the heartbeat of the patient.

Figure 4:
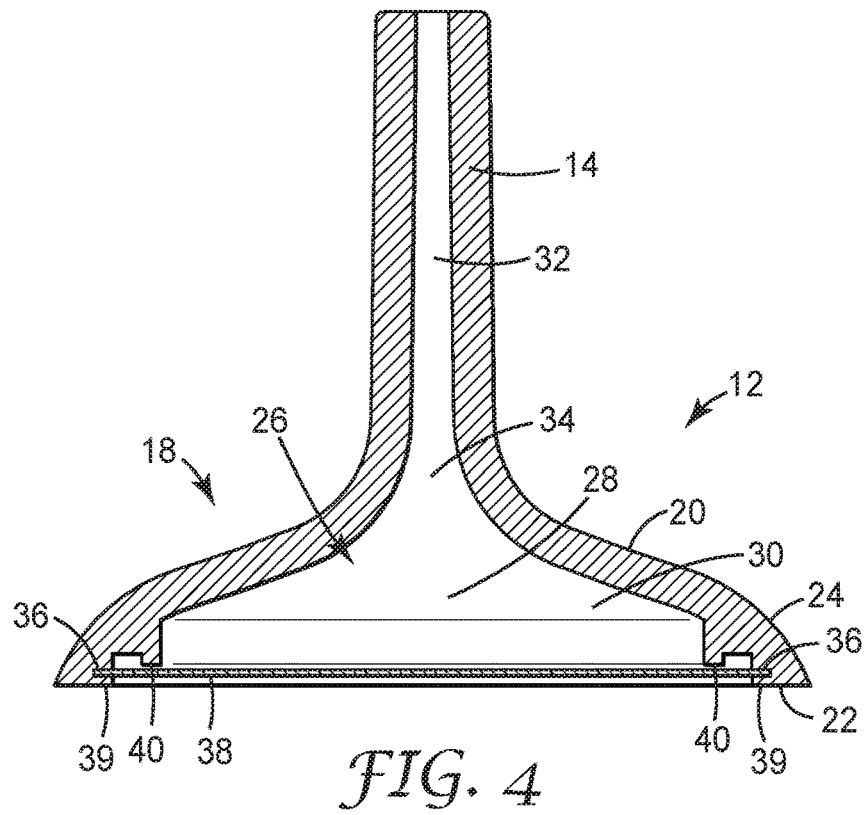
FIG. 4 is a cross-sectional view of the chest piece of the low cost, single-use or single-patient stethoscope of the present invention.
Figure 5:
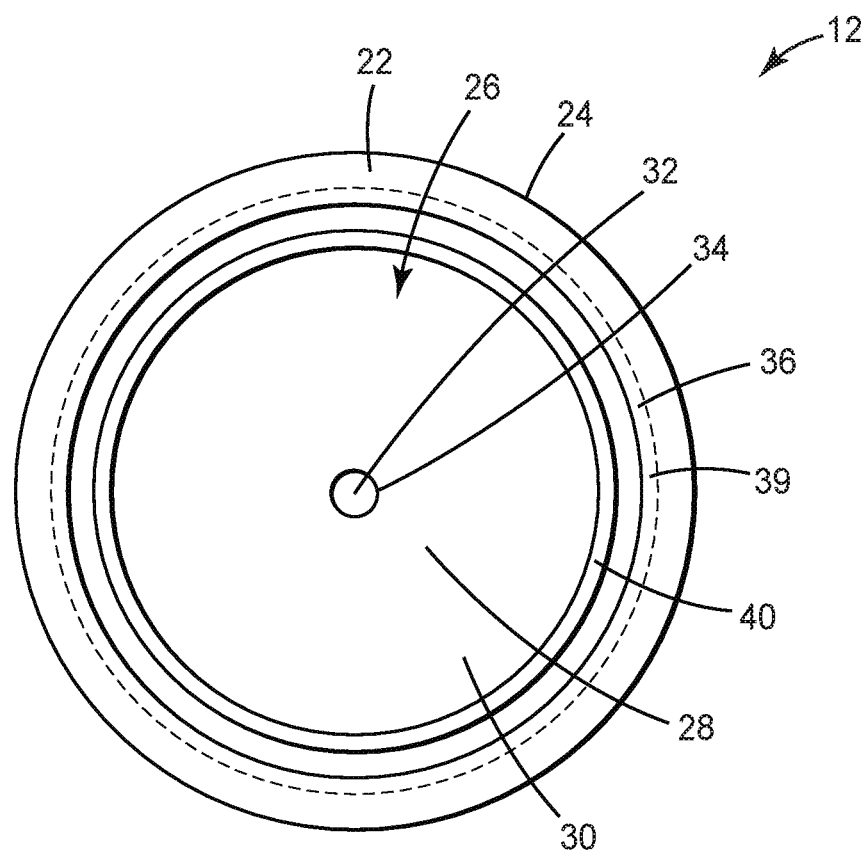
FIG. 5 is a bottom view of the chest piece of the low cost, single-use or single-patient stethoscope of the present invention.

FIG. 4 shows a cross-sectional view of the chest piece 12 and FIG. 5 shows a bottom view of the chest piece 12. Within the dome 18 is an inner dome area 26. The inner dome area 26 of the chest piece 12 affords tuning in of sound and includes an innermost central portion 28, an outer portion 30, and an acoustic channel 32 communicating with the central portion 28. The central portion 28 and acoustic channel 32 are connected by an opening 34. In one embodiment, the opening 34 has a diameter of between about 0.07 inches (1.78 mm) and 0.25 inches (6.35 mm), particularly between about 0.1 inches (2.54 mm) and about 0.2 inches (5.08 mm), and more particularly about 0.156 inches (3.96 mm). Sound travels from the central portion 28 and outer portion 30, through the opening 34 and acoustic channel 32 into the tubing 14 and the ear tips 16 of the stethoscope 10.

Also within the inner dome area 26 is a groove 36 extending along the entire inner circumference of the dome 18 proximate the bottom surface 22 of the chest piece 12. The groove 36 is used to maintain a diaphragm 38 in place within the inner dome area 26 by inserting outer edges of the diaphragm 38 within the groove 36, creating a "floating" diaphragm. The groove 36 creates lip 39, or shelf, that the outer edges of the diaphragm 38 sits within and has an inner diameter $D_I$ and an outer diameter $D_O$. The distance between the inner diameter $D_I$ and the outer diameter $D_O$ is large enough to securely hold the outer edges of the diaphragm 38 in place. In one embodiment, for a diaphragm having a diameter of about 1.72 inches (43.69 mm) and a chest piece having a bottom surface 22 diameter of about 1.9 inches (48.26 mm), the groove 36 has an inner diameter $D_I$ of about 1.6 inches (40.64 mm) and an outer diameter $D_O$ of between about 1.82 inches (46.23 mm) and about 1.67 inches (42.42 mm), and particularly about 1.7 inches (43.18 mm). The groove 36 also has a thickness that allows a friction fit of the diaphragm 38 within the inner dome area 26. In one embodiment, to hold a diaphragm having a thickness of about 0.01 inches (0.25 mm), the groove 36 has a thickness of between about 0.002 inches (0.05) and about 0.030 inches (0.76 mm), particularly between about 0.003 inches (0.08 mm) and about 0.02 inches (0.51 mm), more particularly between about 0.004 inches (0.10 mm) and about 0.01 inches (0.25 mm), and even more particularly about 0.005 inches (0.13 mm).

One particular advantage of using the groove 36 to maintain the diaphragm 38 within the chest piece 12 is that the need for a rim is eliminated. As previously mentioned, conventional chest pieces maintain the diaphragm to the chest piece by use of a rim. The elimination of a rim reduces both cost and the use of resources. The groove 36 is created within the inner area of the dome 26 such that when in use, the diaphragm 38 can contact the patient when the chest piece 12 is placed in contact with the patient and pressure is applied. To ensure that the diaphragm 38 comes into contact with the patient, the groove 36 is positioned in close proximity to the bottom surface 22 of the chest piece 12. In one embodiment, the groove 36 is positioned between about 0.005 inches (0.13 mm) and about 0.175 inches (4.45 mm) from the bottom surface 22, particularly between 0.01 inches (0.25 mm) and about 0.1 inches (2.54 mm) and more particularly at least 0.022 inches (0.56 mm) from the bottom surface 22.

The diameter of the diaphragm 38 may be substantially similar to, less than, or greater than the diameter of the groove 36. When the diameter of the diaphragm 38 is less than the diameter of the groove 36, the diameter of the diaphragm 38 may be up to about 0.1 inches (2.54 mm) greater than the diameter of the groove 36. Preferably, the diameter of the diaphragm 38 is greater than the diameter of the groove 36 prior to the diaphragm 38 being positioned within the groove 36. In one embodiment, for a diaphragm having a diameter of about 1.72 inches (43.69 mm), the diameter of the groove 36 is about 0.050 inches (1.27 mm) smaller, and particularly about 0.020 inches (0.51 mm) smaller than the diameter of the diaphragm 38. In one embodiment, a ratio of the diameter of the diaphragm 38 to the diameter of the groove 36 prior to the diaphragm 38 being positioned within the groove 36 is between about 0.97 and about 1.06. In another embodiment, the diaphragm 38 has a thickness that is greater than the thickness of the groove 36 prior to the diaphragm 38 being positioned within the groove 36. In one embodiment, for a diaphragm having a thickness of about 0.01 inches (0.25 mm), the groove 36 has about one half the thickness of the diaphragm 38. For example, when the thickness of the diaphragm 38 is about 0.01 inches (0.25 mm) thick, the groove 36 is about 0.005 inches (0.13 mm) thick. These relative dimensions in part ensures that the diaphragm 38 remains within the groove 36. Another advantage of the diaphragm 38 having a diameter greater than the diameter of the groove 36 prior to being positioned within the groove 36 is that an airtight seal is created within the inner dome area 26, resulting in improved acoustic performance of the chest piece 12.

The diaphragm 38 may be formed of any material which is known in the art as being suitable for use as a stethoscope diaphragm. Examples of suitable materials include plastics such as polyester, fiberglass-reinforced plastics, and polystyrene and metals such as stainless steel. A suitable thickness for the diaphragm 38 is between about 0.002 inches (0.05 mm) and about 0.03 inches (0.76 mm), particularly between about 0.001 inches (0.03 mm) and about 0.02 inches (0.51 mm), and more particularly about 0.01 inches (0.25 mm).

Similarly to the shape of the chest piece 12, while the specification describes, and the figures depict, the diaphragm 38 the specification describes and as being circular, the diaphragm may be of any two-dimensional shape known to those of skill in the art, such as, for example oval shaped. The shape of the diaphragm 38 must be adjusted to fit the shape of the chest piece 12 opening at the bottom surface 22, without compromising acoustic quality and ease of installment of the diaphragm.

The diaphragm 38 is moveably connected to or "operatively associated" with the bottom surface 22 of the chest piece 12. The diaphragm 38 is positioned within the chest piece 12 such that there can be movement of the diaphragm 38 in a direction substantially perpendicular to the plane of the diaphragm 38 between: 1) a normal outer position to which the diaphragm 38 is biased and 2) an inner position more closely adjacent the central portion 28 of the inner dome area 26. This movement is accomplished without substantially changing the surface contour of or the lateral tension in the diaphragm 38.

The low cost, single-use or single-patient stethoscope 10 of the present invention may further include an optional attenuation ring 40, allowing for frequency-tunable stethoscope. The attenuation ring 40 is located within the inner dome area 26. Together with the central portion 28 of the inner dome area 26, the attenuation ring 40 forms a shallow protrusion within the inner dome area 26. The attenuation ring 40 is sized and shaped to be contacted by the diaphragm 38 when the diaphragm is in the inner position. In one embodiment, the attenuation ring 40 has an inner diameter of between about 0.785 inches (19.94 mm) and about 1.485 inches (37.72 mm), particularly between about 1 inch (25.40 mm) and about 1.3 inches (33.02 mm), and more particularly about 1.185 inches (30.10 mm). In one embodiment, the attenuation ring 40 has an outer diameter of between about 0.985 inches (25.02 mm) and about 1.685 inches (42.80 mm), particularly between about 1.2 inches (30.48 mm) and about 1.5 inches (38.10 mm), and more particularly about 1.385 inches (35.18 mm). In one embodiment, the attenuation ring 40 has a thickness of about 0.1 inches (2.54 mm).

When the diaphragm 38 is in the inner position, the attenuation ring 40 immobilizes the diaphragm 38. To allow movement of the diaphragm 38 within the inner dome area 26 between the outer and inner positions, the attenuation ring 40 is spaced a distance from the diaphragm 38 when in the diaphragm 38 is in the rest, or outer position. In one embodiment, the attenuation ring 40 and diaphragm 38 are spaced between about 0.002 inches (0.05 mm) and about 0.04 inches (1.02 mm) apart from one another, particularly between about 0.01 and about 0.025 inches (0.25 and about 0.64 mm) apart from one another, and more particularly about 0.015 inches (0.38 mm) apart from one another when the diaphragm 38 is in the outer position.

Figure 6:
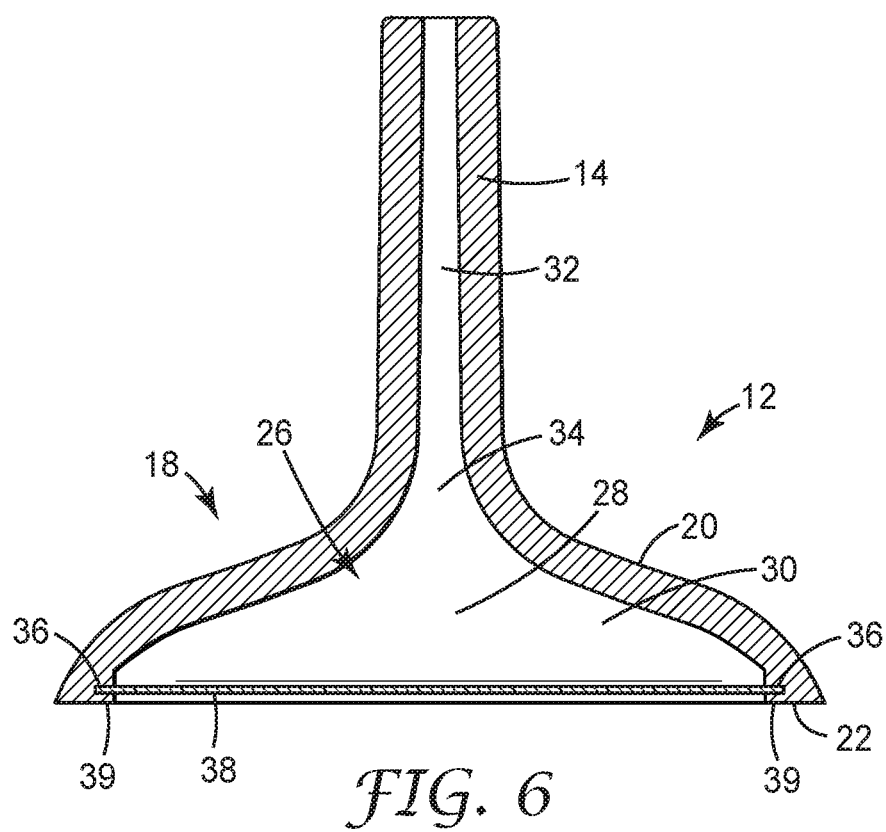
FIG. 6 is a cross-sectional view of another embodiment of the chest piece of the low cost, single-use or single-patient stethoscope of the present invention

FIG. 6 shows a cross-sectional view of the chest piece without an attenuation ring.

The chest piece 12 will pass low frequency (bass) sounds and gradually attenuate sounds with higher frequencies when the diaphragm 38 is in the outer position and between the outer and inner positions. When the diaphragm 38 is in the inner position, the acoustical stiffness of the diaphragm 38 will be significantly higher than the acoustical stiffness of the diaphragm 38 when it is in the outer position, so that the chest piece 12 will attenuate or block low frequency sounds while leaving higher frequency sounds unchanged. In use, a physician would simply modify the manual pressure exerted on the chest piece 12 in order to switch between the outer and inner positions. In one embodiment, the level of bass attenuation varies from about 3 to about 21 dB.

The response of chest piece 12 to low frequency and high frequency sounds is affected by several parameters. For example, the thickness of diaphragm 38 affects the response and suitable thicknesses for diaphragm have been discussed hereinabove. Also, the relative dimensions of inner dome area 26 affect the response.

The ear tips 16 are sized and shaped to engage the surfaces of the user's ears. The ear tips 16 may include any suitable ear tips. In one embodiment, the ear tips 16 include the soft ear tips disclosed in U.S. Pat. Nos. 4,852,684; 4,913,259 and 5,449,865 (the entire contents hereby incorporated by reference).

Process

The dip-molding process that can be used to form the chest piece 12 and tubing 14 of the low cost, single-use or single-patient stethoscope 10 of the present invention is known to those of skill in the art. For example, it is widely used for coating articles with a layer of protective material, including vinyl plastics. Its use in fabricating the flexible tubings of stethoscopes is also known. For example, the dip-molding process is used in the manufacture of currently available stethoscopes, such as those sold under the trademark "Littmann" by 3M Company. The procedure is also specifically mentioned in U.S. Pat. Nos. 3,437,172, and 4,200,169 (the entire contents of which are hereby incorporated by reference).

A feature of dip-molding is the ability to introduce the coating material in its liquid state (e.g., polyvinyl chloride (PVC) before curing) into intimate contact with the article to be coated. The coating material is flowable and can reach small shapes and recesses, and can conform accurately to small changes in dimension, intentional or unintentional, in the article to be coated. This allows detailed forming of features like the attenuating ring and the groove to hold the diaphragm. Also due to this flowable feature, dip-moldings are also desirable to effect an audio-leak-proof coupling between the ear tubes and the flexible tubes of stethoscopes simply by molding the inner diameter of the flexible tube (PVC tubes) slightly smaller than the outer diameter of the ear tubes causing a press fit between the two.

There are a number of variables that enter into obtaining a specific dip mold. These variables include the composition of the PVC being used; the temperatures of the articles being coated and the mandrels being used, and their heat capacities; the curing cycle used; and so on. The assembly used for dip molding, once heated, is dipped into a PVC to the desired depth on the tool/mandrels. The dipped assembly is then withdrawn from the PVC, bearing a coating which is subsequently fully cured, e.g., in an oven. The mandrel is then withdrawn from the assembly leaving smooth-bore tubing and an integrally formed chest piece, where it had been coated with PVC. Appropriate trimming and finishing operations are then done.

The complete process of dip-molding a stethoscope of the present invention is summarized in the following steps:

1. Assemble the chest piece portion of the mandrel onto the tubing portion of the mandrel forming the complete mandrel assembly.
2. Place the mandrel assembly into a preheat oven for preheating until the mandrel is at the desired temperature.
3. Remove the mandrel assembly from the preheat oven and dip it to the desired level in liquid PVC.
4. Remove the assembly from the liquid PVC and place it into the cure oven at a desired temperature for a set period of time.
5. Remove the assembly from the oven and allow it to cool so the cured but hot PVC hardens to a workable state.
6. Trim excess/unwanted PVC off the bottom of chest piece portion of the mandrel assembly.
7. Pull the chest piece portion of the mandrel out the bottom end of the PVC and the tubing/lumen portion of the mandrel out of the top of the PVC, thereby leaving the lumen /tubing and integrally formed chest-piece.
8. The tubing with integrally formed chest piece is now ready to receive the ear tubes with springs and diaphragm.

The process variables include the type and temperature of PVC, time and temperature of the preheat, dipping time, and the time and temperature of the oven curing. The inner surface finish of the lumen of the tube and chest-piece is dependent on the surface finish of the mandrel. The wall thickness is determined by the curing rate and temperature of the PVC and the amount of heat in the mandrel. The amount of heat in the mandrel is determined by the preheat temperature, the cross-sectioned area of the mandrel and the heat capacity of the mandrel material.

EXAMPLES

The present invention is more particularly described in the following examples that are intended as illustrations only, since numerous modifications and variations within the scope of the present invention will be apparent to those skilled in the art. Unless otherwise noted, all parts, percentages, and ratios reported in the following example are on a weight basis.

Example 1

The PVC coating material, Plastisol Blending Resin (Lakeside Plastics Inc., Oshkosh, Wis.) is plasticized with a mixture of dioctyl phthallate (25%) and Santicizer 160 (Monsanto) (75%) in a ratio (plastisol:plasticizer) of 50:50 and is held in a suitable tank at a temperature of about 80° F. The tooling mandrels, for example the mandrel/ear tube assembly are preheated to 300°-400° F. and then are dipped into the tank of liquid plastisol to a depth to achieve he proper length of flexible tubings 14a and 14b. The coated assembly is withdrawn and is transferred to a curing oven at 300°-400° F. The resin cures over a 5-10 minute period to give a smooth, shiny external finish. The mandrels are removed, leaving the cured resin as the flexible tubular body of a low cost, single-use or single-patient stethoscope of the present invention. For Example 1, the mandrel was designed to create a chest-piece and integrally molded stethoscope tubing of the present invention with the following dimensions listed in Table 1 and a resulting shape similar to FIG. 7. For Example 1, the mandrel was designed to create a chest-piece and integrally molded stethoscope tubing of the present invention with the following dimensions listed in Table 1.

TABLE 1

| Component name | Component number as described above and in FIGS. 2-5 | Approximate Dimension (inches) | Approximate Dimension (millimeters) |
|---|---|---|---|
| Opening diameter | 34 | 0.156 | 3.96 |
| Tubing wall thickness | 14 | 0.125 | 3.18 |
| Chest-piece wall thickness | 20 | 0.200 | 5.08 |
| Chest-piece wall thickness | 24 | 0.188 | 4.78 |
| Groove thickness | 36 | 0.005 | 0.13 |
| Lip thickness | 39 | 0.220 | 5.59 |
| Outer diameter of groove | $D_O$ | 1.700 | 43.18 |
| Inner diameter of groove | $D_I$ | 1.600 | 40.64 |
| Diaphragm | 38 | 1.720 | 43.69 |

Examples 2-6

Examples 2-6 were prepared in the same manner as Example 1 with modification to the mandrel so that the groove outer diameter was changed. This was done by using ring-type washers of different sizes to change the groove outer diameter as described in Table 2.

TABLE 2

| Example | Groove 36 outer diameter $D_O$ (inches) | Groove 36 outer diameter $D_O$ (millimeters) | Groove 36 outer diameter $D_O$ change from Example 1 (inches) | Groove 36 outer diameter $D_O$ change from Example 1 (millimeters) |
|---|---|---|---|---|
| Ex. 1 | 1.700 | 43.18 | 0 | 0 |
| Ex. 2 | 1.710 | 43.43 | +0.010 | +0.25 |
| Ex. 3 | 1.720 | 43.69 | +0.020 | +0.51 |
| Ex. 4 | 1.690 | 42.93 | −0.010 | −0.25 |
| Ex. 5 | 1.680 | 42.67 | −0.020 | −0.51 |
| Ex. 6 | 1.670 | 42.42 | −0.030 | −0.76 |

Example 7

Figure 4A:
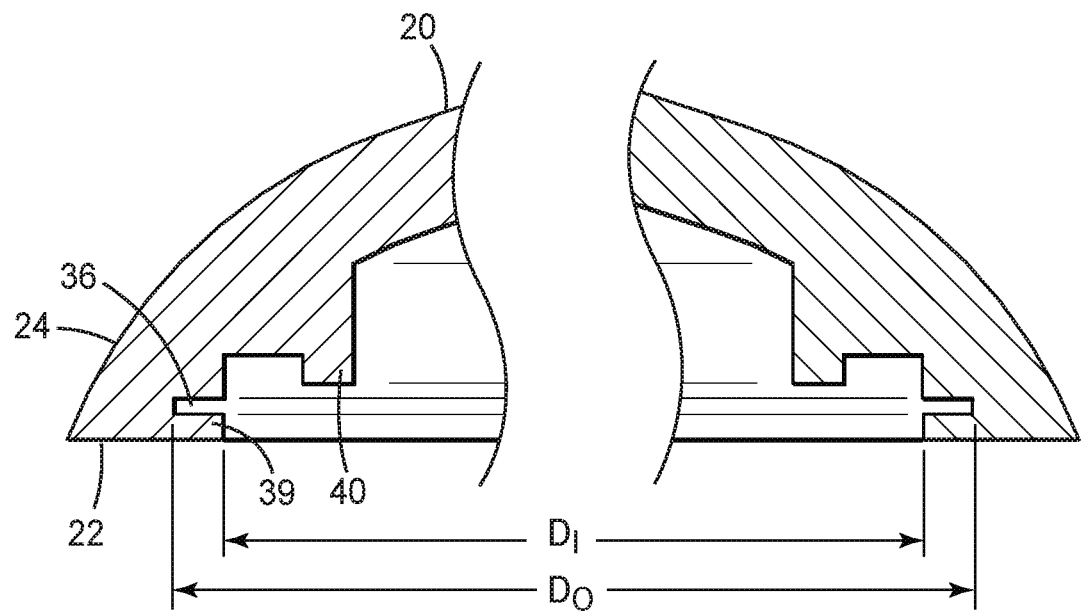
FIG. 4A is an enlarged, cross-sectional view of an edge portion of the chest piece of the low cost, single-use or single-patient stethoscope of the present invention.

Example 7 was prepared in the same manner as Example 1 with modification to the mandrel to create a dip-molded chest-piece with an attenuating ring 40, such as that depicted in FIGS. 4 and 4A. The attenuating ring had an inner diameter of 1.185 inches (30.10 mm), an outer diameter of 1.385 inches (35.18 mm), and a lateral width of 0.100 inches (2.54 mm). The distance between the interior surface of the diaphragm and the face of the attenuating ring was approximately 0.015 inches (0.38 mm).

All the examples used a diaphragm equivalent to those used in 3M™ Littmann® Cardiology II stethoscopes.

Stethoscope Acoustic Testing Apparatus and Procedure

Figure 7:
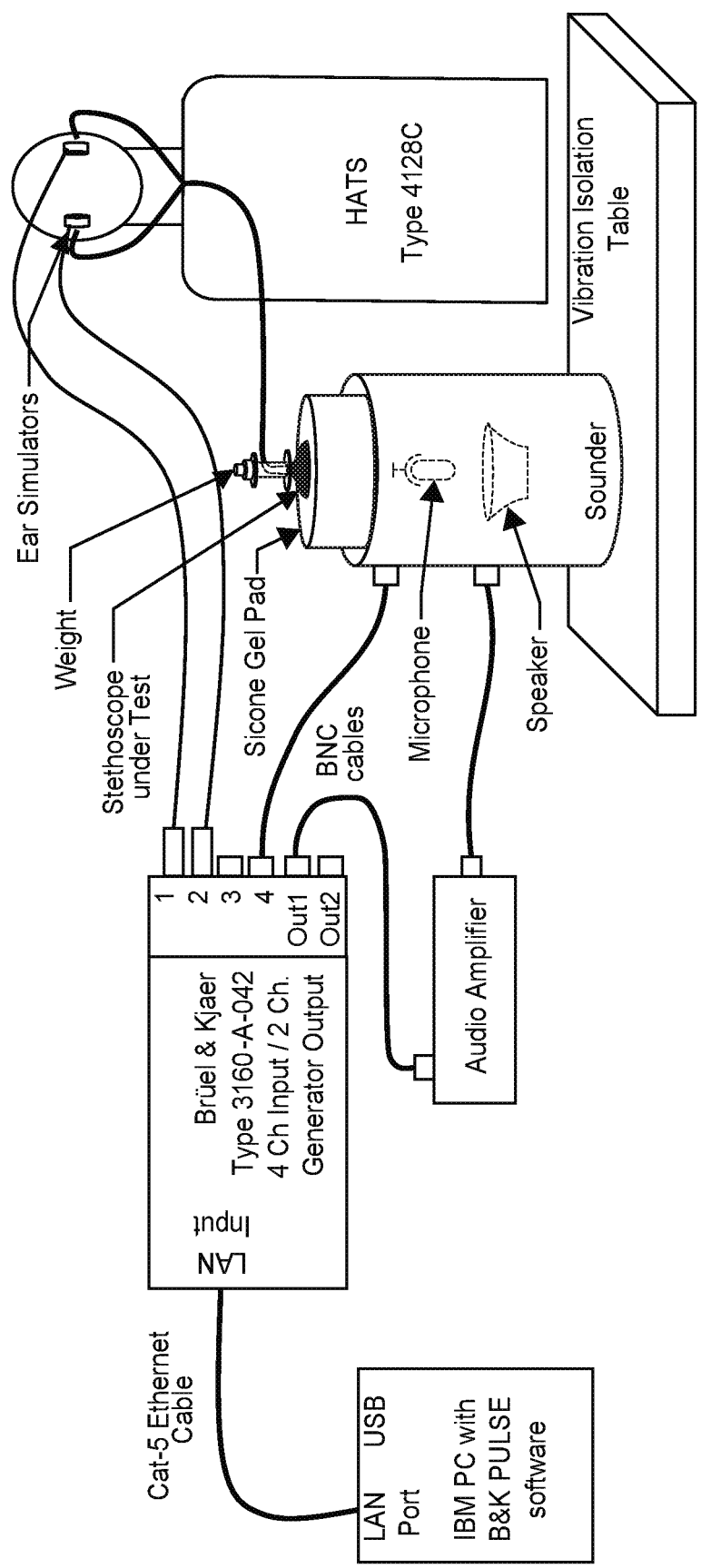
FIG. 7 is a diagram of a laboratory test set-up to generate a transfer function frequency response of stethoscopes using the low cost, single-use or single-patient stethoscope of the present invention.

Acoustic performance of a stethoscope can be described in terms of its frequency response to a broadband or pink noise source coupled to the chest piece in a manner that simulates the human torso. The test apparatus used to characterize the acoustic performance of the examples is illustrated in FIG. 7. The equipment included: a Brüel & Kjær Head and Torso Simulator (HATS) type 4128C with 4159C Left Ear Simulator, 4158C Right Ear Simulator, and Calibrated Left and Right pinnae. The sound source was a loudspeaker enclosed in a cylindrical sounder chamber with an 87 millimeter opening on top filled by a silicone gel pad with dimensions of 130 millimeters diameter×30 millimeters thick. A reference microphone was positioned above the loudspeaker inside the sounder chamber. The signal from this reference microphone was used in the computation of the transfer function frequency response. The silicone gel pad was used to simulate human skin/flesh and was made from ECOLFEX 00-10 Super Soft Shore 00-10 Platinum Silicone Rubber Compound, available from Reynolds Advanced Materials of Countryside, Ill., USA. The low cost, single-use or single-patient stethoscope of Examples 1-6 with an attached diaphragm was placed on the gel pad. A light weight (115 grams) was applied to the top of the chest piece before testing. In a similar manner, the low cost, single-use or single-patient stethoscope of Example 7, with an attached diaphragm, was placed on the gel pad. For Example 7, the applied weight ranged from a light (100 grams) to a firm (900 grams) force that simulated the force applied by a stethoscope user (clinician) to induce the tunable feature of the diaphragm of the stethoscope. The stethoscope ear tips were inserted into the ears of a Head simulator. Microphones in the ear couplers detected the stethoscope sound as in a manner equivalent to the human ear.

Sounds were generated, recorded and characterized by a Brüel & Kjaer (B&K) LAN-XI acoustic test system which operates with a PC using B&K PULSE software. An audio amplifier was used to drive the loudspeaker with sound produced by the LAN-XI system. The sounder cylinder with speaker and reference microphone inside was positioned on a 600 millimeter×900 millimeter Newport IsoStation Vibration Isolation Workstation. A transfer function frequency response curve was generated for each example with various weights used to apply a force to the chest-piece resting on the gel pad. Results are shown in FIGS. 8 and 9.

Figure 8:
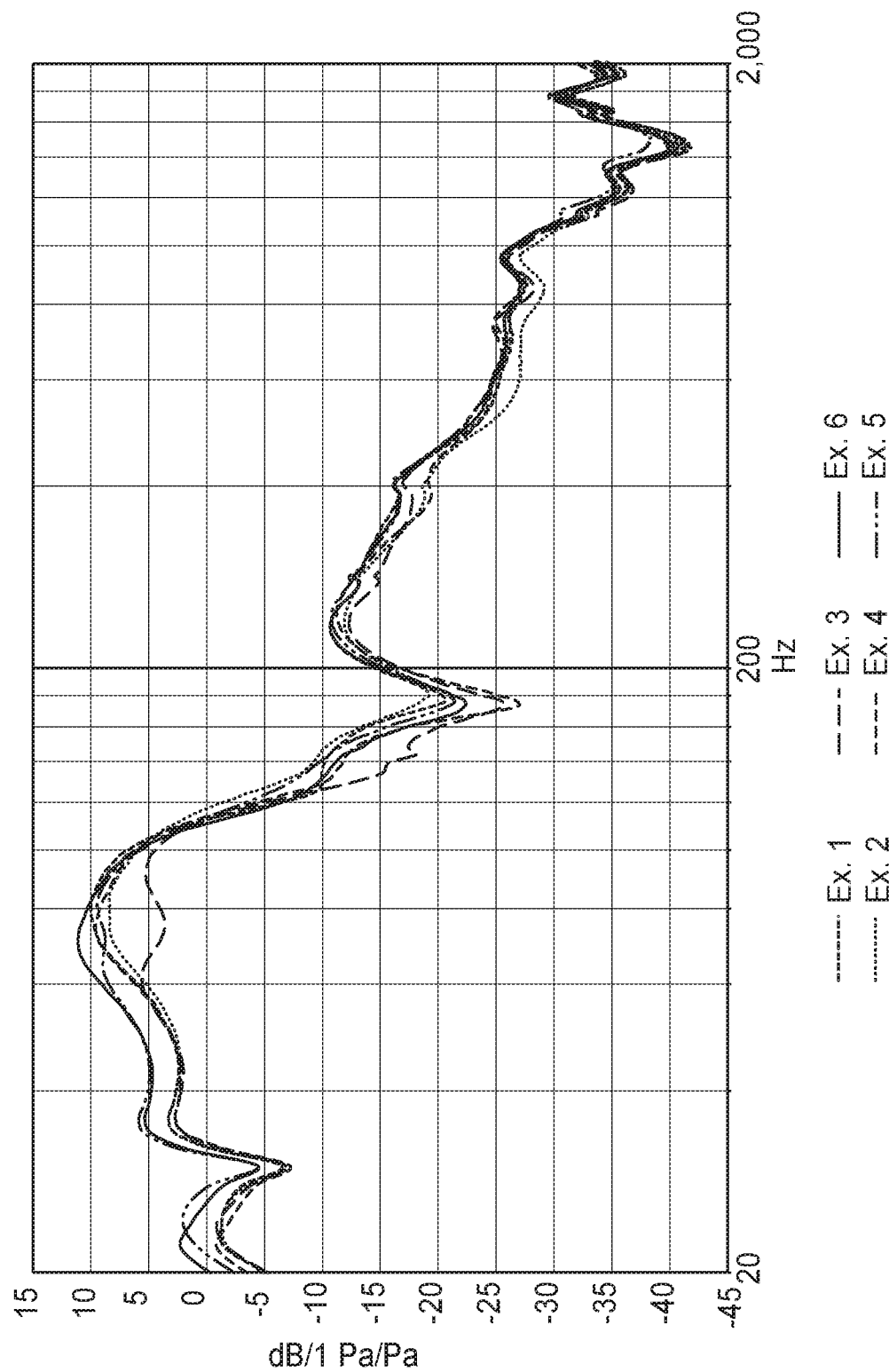
FIG. 8 is a graph showing the transfer function frequency response curves for Examples 1-6.

FIG. 8 is a graph showing the transfer function autospectrum frequency response curves for Examples 1-6. It can be observed in FIG. 8 that at frequencies below 70 Hz, the acoustics were louder for the stethoscopes with a groove diameter 0.2 inches (5.08 mm) and 0.3 inches (7.62 mm) smaller than the diaphragm diameter.

Figure 9:
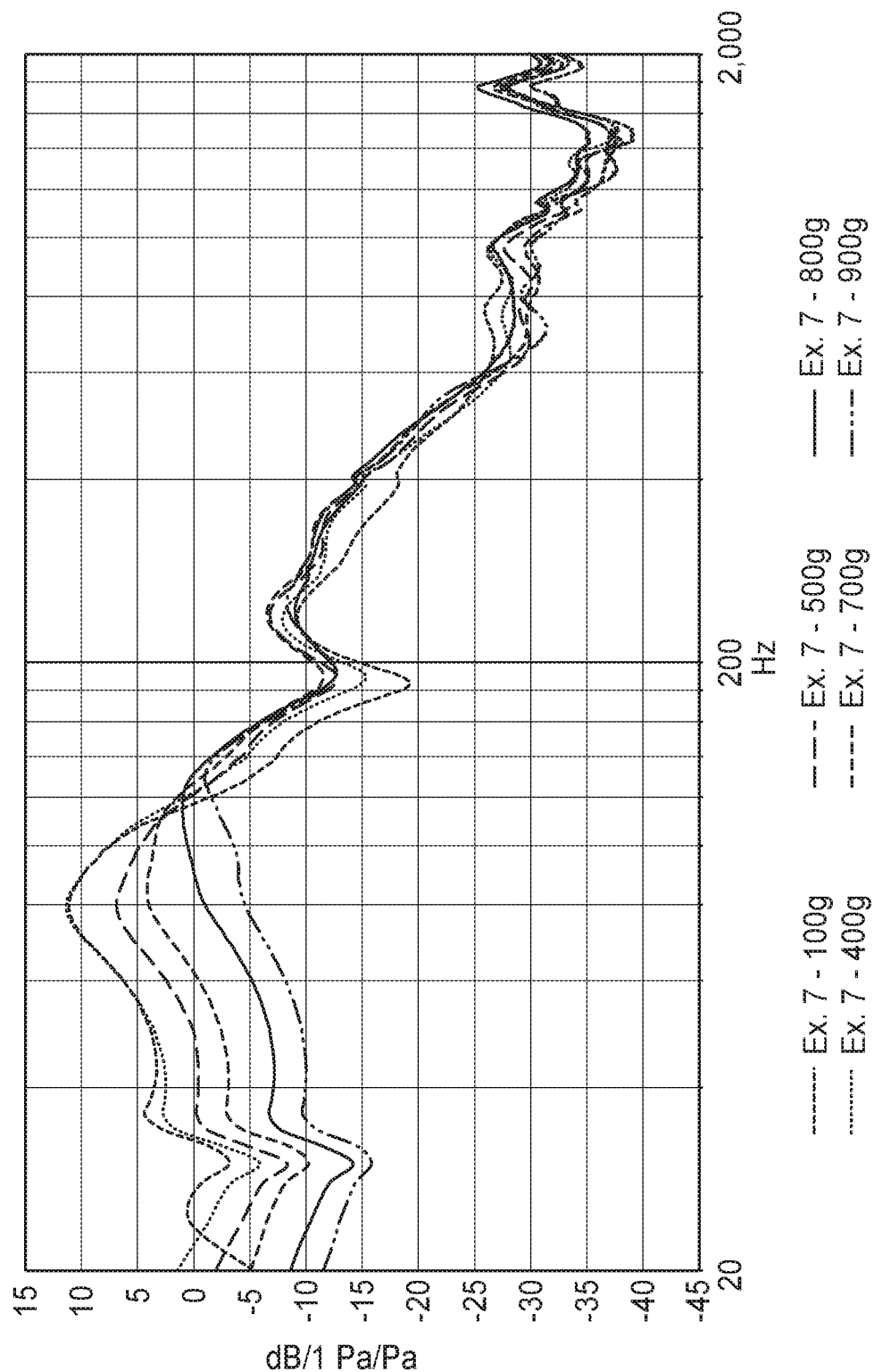
FIG. 9 is a is a graph showing the transfer function frequency response curves for Examples 7 with 100 grams, 400 grams, 500 grams, 700 grams, 800 grams, and 900 grams weights, respectively.

FIG. 9 is a is a graph showing the transfer function autospectrum frequency response curves for Example 7 with 100 grams, 400 grams, 500 grams, 700 grams, 800 grams, and 900 grams weights, respectively.

Although the present invention has been described with reference to preferred embodiments, workers skilled in the art will recognize that changes may be made in form and detail without departing from the spirit and scope of the invention.

What is claimed is:

1. A stethoscope comprising:
    a flexible chest piece having a Shore A durometer hardness of between 30 and 100, comprising:
        a top surface;
        a bottom surface;
        a side surface defining a slope between the top surface and the bottom surface; and
        a horizontal groove extending outwardly toward the side surface and along an inner circumference of the chest piece; and
    a diaphragm positioned within the horizontal groove such that the diaphragm is held in place by the horizontal groove and is recessed from the bottom surface.

2. The stethoscope of claim 1, wherein the flexible chest piece is formed of a polymeric material.

3. The stethoscope of claim 1, wherein a thickness of the diaphragm is greater than a thickness of the groove prior to the diaphragm being positioned within the groove.

4. The stethoscope of claim 1, wherein a diameter of the diaphragm is greater than a diameter of the groove prior to the diaphragm being positioned within the groove.

5. The stethoscope of claim 4, wherein a ratio of the diameter of the diaphragm to the diameter of the groove prior to the diaphragm being positioned within the groove is greater than 1 and no greater than 1.06.

6. The stethoscope of claim 1, wherein the flexible chest piece further comprises an attenuation ring.

7. The stethoscope of claim 1, wherein the groove is positioned between about 0.005 inches (0.13 millimeters) and about 0.175 inches (4.45 millimeters) from the bottom surface.

8. The stethoscope of claim 1, wherein the diaphragm is semi-rigid.

9. The stethoscope of claim 1, wherein the horizontal groove creates a lip that the outer edges of the diaphragm sits within.

10. The stethoscope of claim 1, wherein the diameter of the diaphragm is up to 0.1 inches greater than the diameter of the horizontal groove.

11. The stethoscope of claim 1, wherein the horizontal groove has about one half a thickness of the diaphragm.

12. An acoustic stethoscope comprising:
    a flexible chest piece comprising:
        a top surface;
        a bottom surface;
        a side surface defining a slope between the top surface and the bottom surface; and
        a groove along an inner circumference of the chest piece, wherein the groove is proximate the bottom surface, wherein the groove is horizontal and extends radially toward the side surface;
    a diaphragm positioned within the groove such that the diaphragm is held in place by the horizontal groove and is recessed from the bottom surface; and
    tubing connected to the top surface of the flexible chest piece, wherein the tubing and the chest piece are a unitary piece.

13. The acoustic stethoscope of claim 12, wherein the flexible chest piece and the tubing are formed of a polymeric material.

14. The acoustic stethoscope of claim 12, wherein at least one of a diameter and thickness of the diaphragm is greater than a diameter or thickness of the groove, respectively, prior to the diaphragm being positioned within the groove.

15. The acoustic stethoscope of claim 12, wherein a ratio of the diameter of the diaphragm to the diameter of the groove prior to the diaphragm being positioned within the groove is between about 0.97 and about 1.06.

16. The acoustic stethoscope of claim 12, wherein the tubing extends substantially perpendicularly from the top surface of the flexible chest piece.

17. The acoustic stethoscope of claim 12, wherein the flexible chest piece further comprises an attenuation ring.

18. The acoustic stethoscope of claim 12, wherein the groove is positioned between about 0.005 inches (0.13 millimeters) and about 0.175 inches (4.45 millimeters) from the bottom surface.

19. The acoustic stethoscope of claim 12, wherein the flexible chest piece and the tubing have a Shore A durometer hardness of between about 30 and about 100.

20. The stethoscope of claim 17, wherein the flexible chestpiece forms an inner dome area and the attenuation ring forms a shallow protrusion within the inner dome area.

21. An acoustic stethoscope comprising:
   a flexible chest piece comprising:
      a top surface;
      a bottom surface;
      a side surface defining a slope between the top surface and the bottom surface; and
      a groove extending radially along an inner circumference of the chest piece wherein the groove is positioned between about 0.005 inches (0.13 millimeters) and about 0.175 inches (4.45 millimeters) from the bottom surface; and
   tubing extending substantially perpendicularly from the top surface of the flexible chest piece.

22. The acoustic stethoscope of claim 21, further comprising a diaphragm positioned within the groove such that the diaphragm is held in place by the groove and is recessed from the bottom surface.

23. The acoustic stethoscope of claim 22, wherein at least one of a diameter and thickness of the diaphragm is greater than a diameter and thickness of the groove, respectively, prior to the diaphragm being positioned within the groove.

24. The acoustic stethoscope of claim 22, wherein a ratio of the diameter of the diaphragm to the diameter of the groove prior to the diaphragm being positioned within the groove is between about 0.97 and about 1.06.

* * * * *